(12) United States Patent
Klankermayer et al.

(10) Patent No.: US 10,682,636 B2
(45) Date of Patent: Jun. 16, 2020

(54) IMMOBILIZED RUTHENIUM-TRIPHOS CATALYSTS FOR SELECTIVE HYDROGENOLYSIS OF AMIDES

(71) Applicant: Eastman Chemical Company, Kingsport, TN (US)

(72) Inventors: Jürgen Klankermayer, Essen (DE); Walter Leitner, Aachen (DE); Andreas Rosen, Aachen (DE); Stefan Westhues, Aachen (DE); Robert Thomas Hembre, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/455,968

(22) Filed: Jun. 28, 2019

(65) Prior Publication Data

US 2020/0001286 A1    Jan. 2, 2020

Related U.S. Application Data

(60) Provisional application No. 62/691,936, filed on Jun. 29, 2018.

(51) Int. Cl.

| | |
|---|---|
| *B01J 31/24* | (2006.01) |
| *B01J 31/22* | (2006.01) |
| *B01J 21/08* | (2006.01) |
| *C07F 7/18* | (2006.01) |
| *C07F 15/00* | (2006.01) |
| *C07D 295/027* | (2006.01) |

(52) U.S. Cl.
CPC .......... *B01J 31/2409* (2013.01); *B01J 21/08* (2013.01); *B01J 31/2269* (2013.01); *B01J 31/2291* (2013.01); *C07D 295/027* (2013.01); *C07F 7/1804* (2013.01); *C07F 7/1876* (2013.01); *C07F 15/0046* (2013.01); *B01J 2231/646* (2013.01); *B01J 2531/821* (2013.01); *B01J 2531/828* (2013.01)

(58) Field of Classification Search
CPC .... B01J 31/2409; B01J 21/08; B01J 31/2269; B01J 31/2291; C07D 295/027; C07F 7/1804; C07F 7/1876; C07F 15/0046
USPC ......................................................... 546/184
See application file for complete search history.

(56) References Cited

U.S. PATENT DOCUMENTS

| | | | | |
|---|---|---|---|---|
| 2012/0046481 A1* | 2/2012 | Barnicki | .................. | B01J 31/24 556/18 |
| 2012/0046500 A1* | 2/2012 | Barnicki | .................. | B01J 31/24 568/864 |
| 2015/0087867 A1 | 3/2015 | Klankermayer et al. | | |
| 2016/0168043 A1 | 6/2016 | Klankermayer et al. | | |
| 2018/0008972 A1* | 1/2018 | Klankermayer | ..... | C07D 307/33 |

FOREIGN PATENT DOCUMENTS

WO    2016/128044 A1    8/2016

OTHER PUBLICATIONS

Bianchini; Chem. Commun., 2001, 479-480. (Year: 2001).*
Buchele; Chem. Commun., 1999, 2165-2166. (Year: 1999).*
Findeis; Dalton Trans. , 2003, 249-254. (Year: 2003).*
Findeis; Eur. J. Inorg. Chem. 2003, 99-110. (Year: 2003).*
Kesanli; Chem. Commun., 2004, 2284-2285. (Year: 2004).*
Schober; Eur. J. Inorg. Chem.1998, 1407-1415. (Year: 1998).*
Seitz; Zeitschrift für Naturforschung B, 1994, 49, 1813-1817. (Year: 1994).*
Seitz; Zeitschrift für Naturforschung B, 1995, 50, 1287-1306. (Year: 1995).*
Westhues; Angew. Chem. Int. Ed. 2016, 55, 12841-12844. (Year: 2016).*
Meuresch; Angew. Chem. Int. Ed. 2016, 55, 1392-1395. (Year: 2016).*
Bianchini; Organometallics 2000, 19, 2433-2444. (Year: 2000).*
Anon., "Catalytic Hydrogenation of Amides," Aug. 2, 2014 (Sat) Ozawa Jun (D1), pp. 1-20.
Int'l Search Report and Written Opinion issued in Int'l Application No. PCT/US2019/031856 filed May 10, 2019.
S. Wesselbaum et al., "Hydrogenation of carbon dioxide to methanol using homogeneous ruthenium-Triphos catalyst: from mechanistic investigations to multiphase catalysis," Chem. Sci., 2015, 6, 693-704.
Copending U.S. Appl. No. 16/409,522 filed May 10, 2019.
Int'l Search Report and Written Opinion issued in Int'l Application No. PCT/US2019/039726 filed Jun. 28, 2019.
R. Kadyrov, "Hydrogenolysis of Amide Acetals and Iminium Esters," ChemCatChem 2018, 10, 170-172.

* cited by examiner

*Primary Examiner* — Daniel R Carcanague
(74) *Attorney, Agent, or Firm* — Phan Law Group PLLC

(57) ABSTRACT

A compound represented by the structure of formula (I):

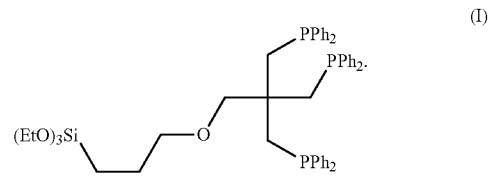

The compound is useful as a ligand for ruthenium to form an organometallic complex. The complex may be immobilized on an oxidic support to form an active, heterogeneous catalyst for the hydrogenolysis of amides to form amines and optionally alcohols.

20 Claims, 1 Drawing Sheet

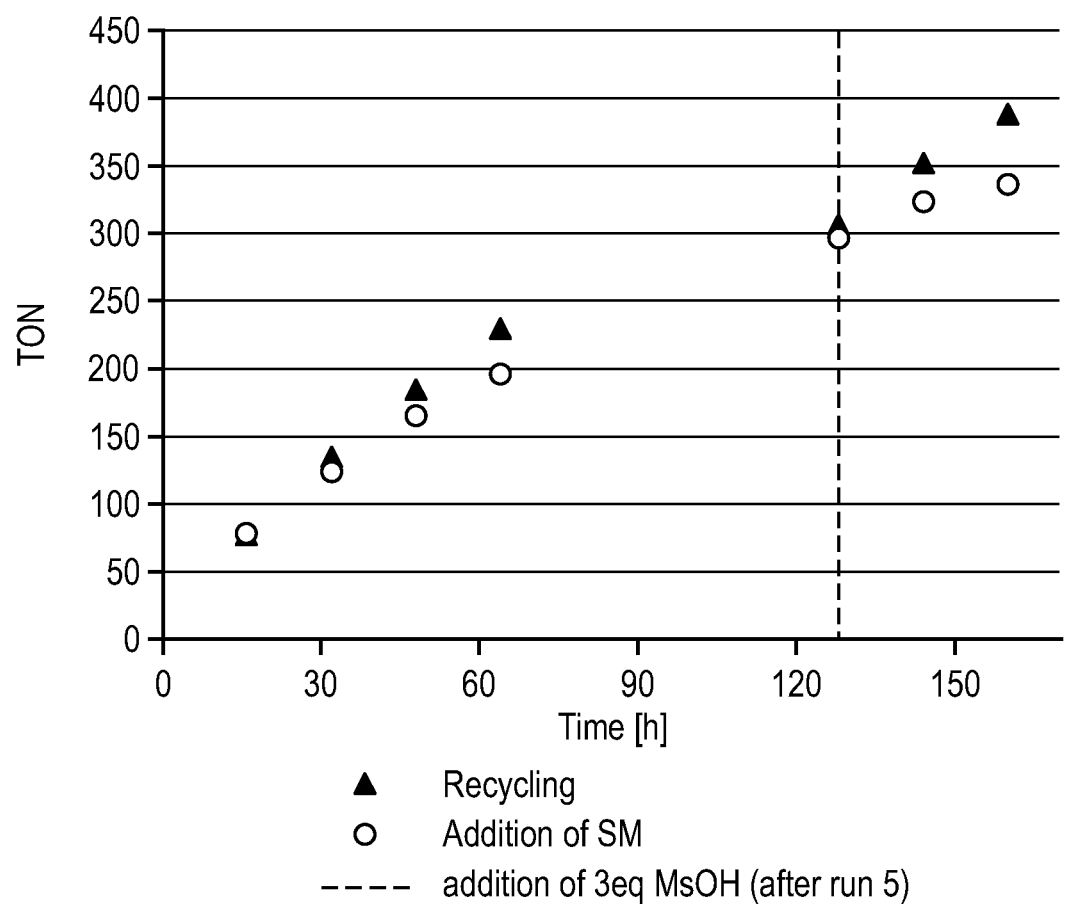

IMMOBILIZED RUTHENIUM-TRIPHOS CATALYSTS FOR SELECTIVE HYDROGENOLYSIS OF AMIDES

CROSS-REFERENCE TO RELATED APPLICATION

This is application claims the benefit of Provisional Application No. 62/691,936 filed on Jun. 29, 2018 under 35 U.S.C. § 119(e)(1); the entire content of the provisional application is hereby incorporated by reference.

FIELD OF THE INVENTION

The invention generally relates to the field of organic chemistry. It particularly relates to silyl ether triphos compounds, organometallic complexes containing the silyl ether triphos compounds, catalysts containing the organometallic complexes immobilized on oxidic supports, methods of making, and/or methods of using the compounds, complexes, and catalysts.

BACKGROUND OF THE INVENTION

The hydrogenolysis of amides to amines under mild reaction conditions represents a challenging chemical transformation and has recently been defined as a high-priority research area of the pharmaceutical industry. Traditionally, stoichiometric amounts of reducing agents, such as $LiAlH_4$, DIBAL, or $NaBH_4$, are required to reduce amides to amines. All of these reducing agents, however, have poor atom economy and produce environmentally dangerous products.

In contrast, elemental hydrogen, the simplest reducing agent, generates only water as a by-product, thus making the reaction more atom economical and environmentally friendly. However, only recently have efficient molecular catalysts been developed for using hydrogen as the reducing agent—paving the way to a more economical, safe, and environmentally benign production of pharmaceuticals.

Despite their development, these molecular catalysts still suffer from various disadvantages, such as the inability to be easily separated and recycled. Moreover, some of them have relatively short lifetimes due to their susceptibility to bimolecular deactivation.

Thus, there is a need in the art to provide alternative and/or improved catalysts and processes for hydrogenolysing amides to form amines and optionally alcohols, particularly ones that do not suffer from one or more of these drawbacks.

The present invention addresses this need as well as others, which will become apparent from the following description and the appended claims.

SUMMARY OF THE INVENTION

The invention is as set forth in the appended claims.

Briefly, in one aspect, the invention provides a compound having the structure of formula (I):

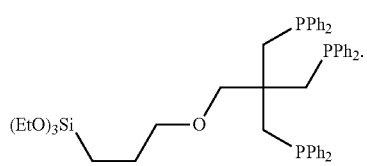

(I)

In another aspect, the invention provides a compound having the structure of formula (II):

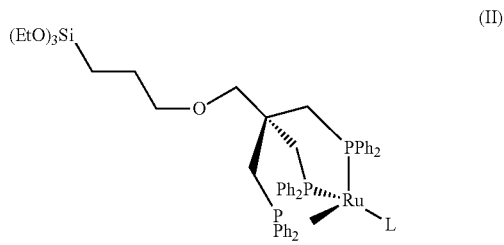

(II)

wherein L represents a leaving group.

In yet another aspect, the invention provides a catalyst composition comprising:
(a) an oxidic support; and
(b) the compound of formula (II) immobilized on the support.

In yet another aspect, the invention provides a process for hydrogenolysing an amide. The process comprises the step of:

contacting an amide with hydrogen in the presence of a catalyst composition at conditions effective to form an amine and optionally an alcohol, wherein the catalyst composition comprises:
(a) an oxidic support; and
(b) the compound of formula (II) immobilized on the support.

BRIEF DESCRIPTION OF THE DRAWINGS

The FIGURE is a graph of the catalyst turnover number (TON) versus time for the recycling and substrate-addition experiments in the hydrogenolysis of 2-piperidone to piperidine in Example 4.

DETAILED DESCRIPTION OF THE INVENTION

In one aspect, the invention provides a compound represented by the structural formula (I):

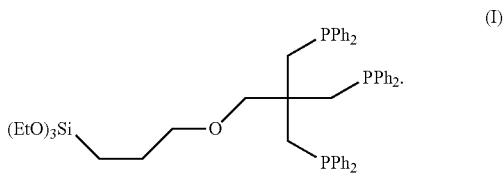

(I)

The compound of formula (I) (or simply compound (I)) contains a triphos group and a triethoxysilyl group linked by a propoxy group. As seen from formula (I), triphos refers to 1,1,1-tris(diphenylphosphinomethyl)ethane.

Compound (I) may be prepared by a method comprising the following steps:

(a) reacting pentaerythritol tribromide with allyl iodide in the presence of a base to form an ether compound having the structure of formula (A):

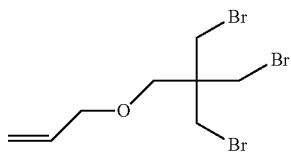

(A)

(b) reacting the ether compound (A) with triethoxysilane in the presence of a platinum-N-heterocyclic carbene (Pt—NHC) catalyst to form a silyl ether compound having the structure of formula (B):

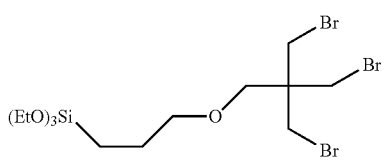

(B)

(c) reacting the silyl ether compound (B) with potassium diphenylphosphide to form the compound of formula (I).

The steps (a)-(c) may be carried out in a compatible solvent. The solvent may be the same or different in each step and is not particularly limiting so long as it can sufficiently dissolve the reactants/base/catalyst. Suitable solvents include non-polar solvents, such as hexane, benzene, and toluene; and polar aprotic solvents, such as tetrahydrofuran (THF) and dimethyl sulfoxide (DMSO).

The base employed in step (a) is also not particularly limiting. Suitable bases include alkali metal alkoxides, such as potassium-tert-butoxide.

Even though various known Pt—NHC catalysts as well as Wilkinson's catalyst (chloridotris(triphenylphosphane)rhodium(I)) can facilitate the reaction of step (b), a Pt—NHC catalyst having the structure of formula (C) is preferred:

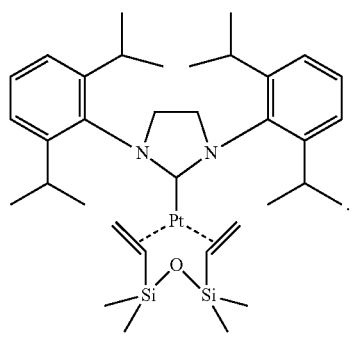

(C)

Catalyst (C) may be prepared by methods known in the art.

The steps (a)-(c) may be carried out at room temperature or at elevated temperatures, such as from 40 to 200° C.

Compound (I) is useful as a ligand for ruthenium to make a compound of the structural formula (II):

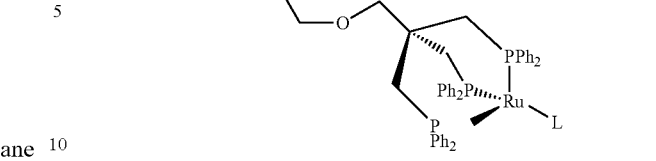

(II)

wherein L represents a leaving group.

Thus, in another aspect, the invention provides an organometallic compound having the structure of formula (II).

The leaving group L represents one or more "volatile" or easily removable ligands, which stabilizes the complex so that it may be handled before the hydrogenolysis reaction, but during the reaction sequence, it is generally replaced by the reactant(s). Examples of such volatile ligands include trimethylenemethane, allyl, methylallyl, ethylene, cyclooctadiene, acetylacetonate, and acetate.

In various embodiments, the leaving group L comprises trimethylenemethane (TMM).

Compound (II) may be prepared by reacting compound (I) with a ruthenium-containing compound.

The Ru-containing compound is not particularly limiting. It can be a salt or a complex containing ruthenium, independent of its formal oxidation state. Suitable Ru-containing compounds include $Ru(acac)_3$, $[Ru(COD)(methylallyl)_2]$, $Ru(NBD)(methylallyl)_2$, $Ru(ethylene)_2(methylallyl)_2$, $[(COD)RuCl_2]_n$, $RuCl_3$, $[(PPh_3)_3Ru(H)(CO)Cl]$, and $[(cymanthren)RuCl_2]_2$.

In various embodiments, the Ru-containing compound comprises $[Ru(COD)(methylallyl)_2]$.

The reaction to form compound (II) may be carried out in a compatible solvent. The solvent is not particularly limiting so long as it can sufficiently dissolve the reactants. Suitable solvents include non-polar solvents, such as hexane, benzene, and toluene.

The reaction to form compound (II) may be carried out at room temperature or at elevated temperatures, such as from 60 to 210° C., from 100 to 200° C., or from 120 to 180° C.

Advantageously, compound (II) can be immobilized on an oxidic support to form a solid or heterogeneous catalyst composition.

Thus, in another aspect, the invention provides a catalyst composition comprising an oxidic support and compound (II) immobilized on the support.

Examples of oxidic supports include magnesia (MgO), titania ($TiO_2$), alumina ($Al_2O_3$), and silica ($SiO_2$). Preferably, the oxidic support comprises silica, in particular amorphous silica.

The amount of compound (II) immobilized on the oxidic support is not particularly limiting. For example, the catalyst composition may contain from 0.01 to 1, from 0.05 to 0.5, or from 0.05 to 0.3 mmol of Ru/g of support.

The catalyst composition may be prepared by methods known in the art. For example, in the case of silica, the catalyst composition may be prepared by first dehydroxylating the silica under vacuum at elevated temperature (e.g., 500° C.) and then refluxing a mixture containing the silica and a solution containing compound (II) in a non-polar solvent, such as toluene, for a period of time (e.g., overnight). The catalyst composition may be recovered from the mixture by filtration.

It has been surprisingly found that the immobilized catalyst containing compound (II) on an oxidic support is particularly effective for catalyzing the hydrogenolysis of amides to form amines and optionally alcohols. This catalyst showed high performance, e.g., in the hydrogenolysis of 2-piperidone to piperidine, as well as long-term stability and low leaching rates.

Thus, in another aspect, the present invention provides a process for hydrogenolysing an amide. The process comprises contacting an amide with hydrogen in the presence of a catalyst composition at conditions effective to form an amine and optionally an alcohol, wherein the catalyst composition comprises compound (II) immobilized on an oxidic support.

It should be noted that not necessarily all of the phosphines are bound to the ruthenium during the reaction. Moreover, not all of the phosphorus atoms may catalytically be involved in the reaction.

The amount of the catalyst used for carrying out the reaction can vary over a wide range. For example, the catalyst loading may range from 0.01 to 10 mol %, from 0.1 to 5 mol %, or from 0.1 to 1 mol %.

The hydrogenolysis process may be carried out in the absence of an added acid.

Alternatively, the hydrogenolysis process may be carried out in the presence of an acid.

In the case one or more acids are used in the hydrogenolysis reaction, the (initial) concentration of acid may range from 0.5 to 20 times the concentration of ruthenium on a molar basis. Other acid concentrations include 0.8 to 10 times, 1 to 5 times, or 1 to 2 times the concentration of ruthenium on a molar basis.

The acid is not particularly limiting. For example, it may be organic or inorganic, such as sulfonic acids, especially methanesulfonic acid, trifluoromethanesulfonic acid, p-toluenesulfonic acid, and sulfuric acid; trifluoroacetic acid; perchloric acid; and mixtures thereof. Other suitable acids include those that provide weak coordinating anions after deprotonation, such as bis(trifluoromethane)sulfonimide ($HNTf_2$) or mixtures thereof with the aforementioned acids.

In various embodiments, the acid may be $HNTf_2$, methanesulfonic acid (MSA), tris(pentafluorophenyl)borane ($B(C_6F_5)_3$), or aluminum trifluoromethanesulfonate ($Al(OTf)_3$).

The hydrogenolysis contacting step is preferably carried out at an elevated temperature, e.g., from 40 to 250° C. Other contacting step temperatures include from 60 to 210° C., from 120 to 200° C., or from 140 to 180° C.

Depending on the amide to be reacted, the process may be performed in the absence of or in the presence of an added solvent. The solvent may be common non-polar solvents, such as aliphatic or aromatic hydrocarbons, or slightly polar, aprotic solvents, such as ethers. Examples of aliphatic solvents include pentanes and hexanes. Examples of aromatic solvents include benzene, xylenes, toluene, and trimethylbenzenes. Examples of ether solvents include tetrahydrofuran, dioxane, diethyl ether, and polyethers.

The contacting step may be carried out at an initial hydrogen pressure of at least 1 bar, at least 10 bar, or at least 20 bar and in each case, up to 1000 bar, up to 750 bar, up to 500 bar, up to 250 bar, or up to 100 bar.

There is no particular restriction on the type of amide that can be converted in the hydrogenolysis process of the present invention. For example, the amide may be primary, secondary, or tertiary, although primary amides may be less selectively reduced than secondary or tertiary amides. In various embodiments, the amide is secondary or tertiary.

Specific examples of amides that can be used in the process of the invention include N-methylacetamide, N,N-dimethylacetamide, N-methylprionamide, N,N-dimethylpropionamide, N-methylisobutyramide, N,N-dimethylisobutyramide, n-methylbutyramide, N,N-dimethylbutyramide, N-methyl valeramide, N,N-dimethylvaleramide, N-methylcaproamide, N,N-dimethylcaproamide, N-methylbenzamide, N,N-dimethylbenzamide, N-methylphenacetamide, N,N-dimethylphenacetamide, 2-ethyl-N-methylhexanamide, 2-ethyl-N,N-dimethylhexanamide, N-methyldecanamide, N,N-dimethyldecanamide, N-hexylcaproamide, N-acetylpyrrolidine, N-acetylpiperidine, N-acetylmorpholine, N-benzyl-2-methoxyacetamide, N-methylglycolamide, N,N-dimethylglycolamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, ethylenediamine-N,N'-(2-methoxyacetamide), N-hexanoylmorpholine, N-butanoylmorpholine, N-2-methoxyacetylpyrrolidine, N-formylmorpholine, N,N-dimethylformamide, N,N-dimethylbenzamide, tetramethyloxamide, N,N,N',N'-tetramethyl-1,4-cyclohexanedicarboxamide, and N,N'-dimethyl-1,4-cyclohexanedicarboxamide.

The process of the invention can also hydrogenolyse cyclic amides, such as x-butyrolactam, δ-valerolactam, ε-caprolactam, piperizin-2-one, cyclodiglycine, cycloglycyl-L-valine, N-methylpyrrolidinone, N-phenylpyrrolidinone, N-ethyl-pyrolidinone, N-butylpyrrolidinone, N-methylpiperidinone, N-methyl-5-methylpiperidinone, N-methylcaprolactam, and N-ethylcaprolactam.

In various embodiments, the amide is δ-valerolactam, N-hexylhexanamide, N-methyldecylamide, or N-dimethyldecylamide.

In various embodiments, the process further comprises the step of removing the product amine from the reaction zone during the hydrogenolysis reaction.

To remove any doubt, the present invention includes and expressly contemplates and discloses any and all combinations of embodiments, features, characteristics, parameters, and/or ranges mentioned herein. That is, the subject matter of the present invention may be defined by any combination of embodiments, features, characteristics, parameters, and/or ranges mentioned herein.

It is contemplated that any ingredient, component, or step that is not specifically named or identified as part of the present invention may be explicitly excluded.

Any process/method, apparatus, compound, composition, embodiment, or component of the present invention may be modified by the transitional terms "comprising," "consisting essentially of," or "consisting of," or variations of those terms.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered as approximations, unless the context indicates otherwise. These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to include all values within the range including sub-ranges such as 60 to 90, 70 to 80, etc.

Any two numbers of the same property or parameter reported in the working examples may define a range. Those numbers may be rounded off to the nearest thousandth, hundredth, tenth, whole number, ten, hundred, or thousand to define the range.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following working examples, although it should be understood that these examples are included merely for purposes of illustration and are not intended to limit the scope of the invention.

EXAMPLES

Example 1

Preparation of [Ru(Silyl-Triphos)TMM]@Silica

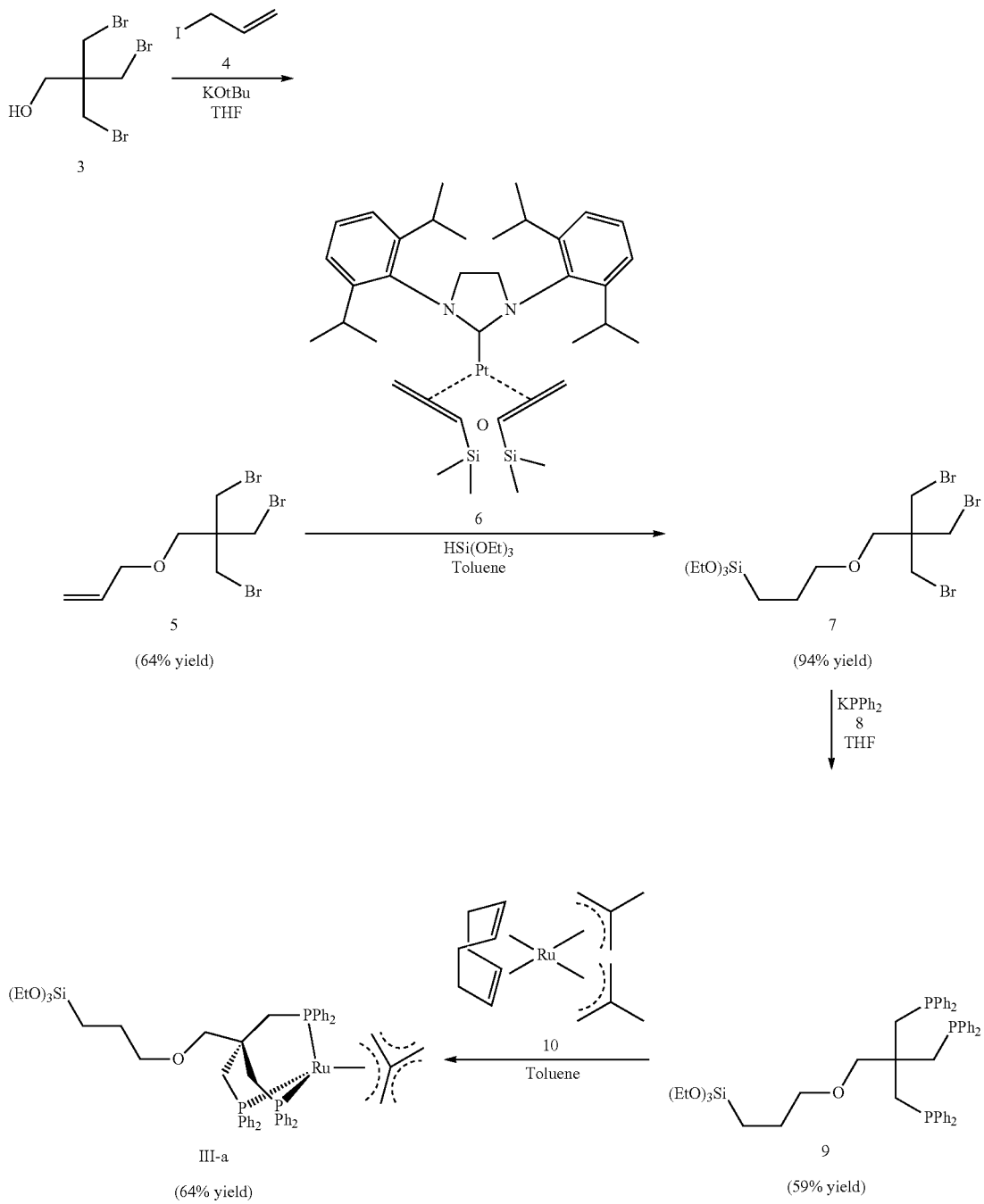

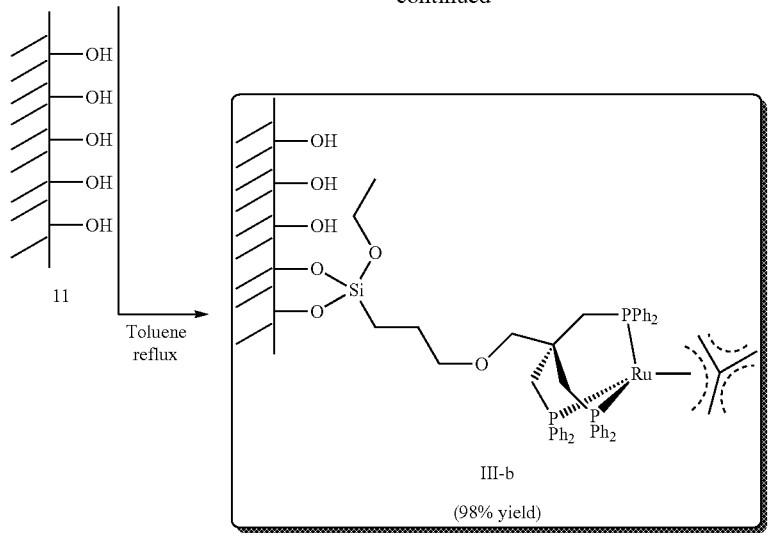

III-b
(98% yield)

Immobilized complex III-b was synthesized according to the scheme above. In particular, the ether 5 was easily accessible from commercially available pentaerythritol tribromide 3 via nucleophilic substitution with allyl iodide 4. Use of the Pt—NHC-catalyst 6 resulted in the conversion of compound 5 to compound 7, which was especially selective for the linear product. Other Pt—NHC catalysts, as well as Wilkinson's catalyst, produced considerably larger amounts of side products. Subsequent reaction of compound 7 with potassium diphenylphosphide 8 gave the modified Silyl-Triphos ligand 9. Complex III-a was obtained by reacting ligand 9 with [Ru(2-methylallyl)$_2$(COD)] 10 using the synthetic protocol described in T. vom Stein et al., *Chem-CatChem* 2013, 5, 439-441.

In order to enforce a single molecularly defined complex on the surface of the support, the grafting of the tailored complex was performed in the last step in the synthesis sequence. The immobilization on silica as a robust and chemically stable material was found to be the most suitable support for phosphine immobilization compared to MgO, TiO$_2$, and Al$_2$O$_3$.

Complex III-a was grafted onto silica 11, which had previously been dehydroxylated under vacuum at 500° C., by refluxing overnight in toluene. The supernatant solution after filtration and washing of catalyst III-b contained no detectable amount of complex III-a by NMR. Elemental analysis by inductively coupled plasma optical emission spectrometry (ICP-OES) showed that the loading of Ru was within error of the theoretical value (SI, 2.6). For comparability reasons, the theoretical loading was used for performing catalysis and analysis.

In the $^{29}$Si cross polarization magic angle spinning (CP-MAS) NMR, the characteristic signals at −57.8 ppm corresponded to the grafted triethoxysilyl functionality, confirming that the complex was covalently attached through the silyl linker. The $^{31}$P-MASNMR of catalyst III-b showed one major species at 31.7 ppm, which is to the free complex III-a. A minor species at 51.3 ppm was also present, which may be a species in which Ru is coordinated directly to the silica surface. The presence of small amounts of isobutene during the grafting supports this assignment. IR spectroscopy showed the characteristic CH-stretching and bending bands of the triphos ligand (SI, 2.6). All these data confirm that catalyst III-b mostly contained [Ru(Silyl-Triphos)(TMM)] complexes covalently linked to the silica surface through the silyl linker.

General Hydrogenolysis Procedure

The catalysts III-b and IV (see below) were weighed under Ar atmosphere in a glass insert designed to fit inside an autoclave reactor and equipped with a stirring bar. If an additive was used, a stock solution of the additive in a solvent was added, and the glass insert was placed in a 10-mL steal autoclave. The autoclave was pressurized at room temperature with 100 bar of hydrogen, placed in an alumina cone, and the suspension was stirred for the specified time at the denoted temperature. Afterwards, the reaction was cooled to ambient temperature and carefully depressurized to atmospheric pressure. Conversion and yield were determined by 1H NMR spectroscopy using mesitylene as internal standard. Leaching rates were determined by ICP-MS.

Example 2

Hydrogenolysis of 2-Piperidone to Piperidine

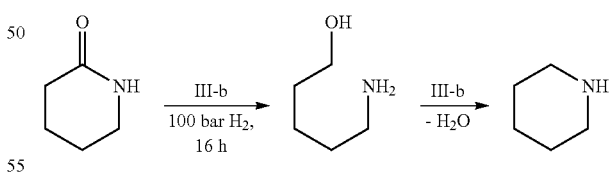

The hydrogenolysis of 2-piperidone to piperidine, as shown in the above equation, was chosen as a benchmark reaction to investigate the catalytic activity and leaching behavior of catalyst III-b in a variety of solvents and under various conditions.

2-Piperidone was subjected to hydrogenolysis in seven experiments according to the general procedure above. The conditions for Runs 1-4 were as follows: 0.25 mol % catalyst loading (0.06 mmol/g on amorphous silica); 1.0 mmol substrate; 1.0 mL solvent; 160° C.; and 100 bar H$_2$ at room temperature. The conditions for Runs 5-7 were the same as Runs 1-4, except that 0.50 mol % catalyst loading was used. The results are shown in Table 1.

TABLE 1

| Run | Solvent | Temp. (° C.) | Conv. (%) | Yield (%) | Ru Leaching (ppm) |
|---|---|---|---|---|---|
| 1 | THF | 160 | 72 | 67 | 0.9 (0.34%) |
| 2 | Dioxane | 160 | 64 | 59 | 1.3 (0.52%) |
| 3 | Toluene | 160 | 74 | 66 | 1.0 (0.38%) |
| 4 | THF | 100 | 8 | 7 | 5.0 (0.99%) |
| 5 | THF | 120 | 37 | 36 | 2.3 (0.44%) |
| 6 | THF | 140 | 72 | 70 | 1.2 (0.24%) |
| 7 | THF | 160 | 95 | 91 | 1.5 (0.26%) |

As seen from Table 1, THF and toluene were the best solvents for this transformation, having the best conversions (up to 95%) and the lowest leaching rates (between 0.24 and 0.99% total Ru leaching). Almost full conversion was observed at 160° C. using 0.5 mol % of catalyst III-b (Run 7). Lower temperatures drastically decreased the yields. Surprisingly, lower temperatures also resulted in more leaching.

Without wishing to be bound by theory, this increase in the leaching rate at lower temperature can be explained by the increased concentration of the intermediate linear amino alcohol, according to the presented reaction mechanism in this transformation. To test this theory, additional runs were performed with excess intermediate. The data showed that adding excess intermediate resulted in much higher leaching rates. In contrast, adding excess water, similar to what would be made by complete hydrogenolysis of the substrate, did not result in increased leaching (SI, 4).

Example 3

Comparison of Immobilized Versus Non-Immobilized Catalyst

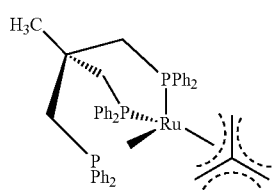

(IV)

Following the general procedures above, 2-piperidone was reduced to piperidine using three catalysts: (1) the homogeneous complex IV ([Ru(Triphos)(TMM)]) (Runs 1-2); (2) complex IV adsorbed on amorphous silica before use (Run 3); and (3) the immobilized catalyst III-b (Runs 4-5). The conditions for the runs were as follows: 1.0 mmol substrate; 1.0 mL THF; 160° C.; and 100 bar H₂ at room temperature. The results are shown in Table 2.

TABLE 2

| Run | Cat. | Loading (mmol/g) | MsOH (equiv.) | Conv. (%) | Yield (%) | Ru Leaching (ppm) |
|---|---|---|---|---|---|---|
| 1 | IV | — | — | 7 | 4 | n.d. |
| 2 | IV | — | 1.5 | 10 | 9 | n.d. |
| 3 | IV@silica | 0.2 | 1.5 | 18 | 11 | n.d. |

TABLE 2-continued

| Run | Cat. | Loading (mmol/g) | MsOH (equiv.) | Conv. (%) | Yield (%) | Ru Leaching (ppm) |
|---|---|---|---|---|---|---|
| 4 | III-b | 0.2 | — | 95 | 91 | 3.5 (0.68%) |
| 5 | III-b | 0.06 | — | 94 | 91 | 1.5 (0.26%) | n.d. = not determined

As seen from Table 2, the immobilized catalyst III-b was tested at two different Ru loadings (Runs 4-5). This catalyst afforded comparably high yields and low leaching rates. Under the same conditions, the homogeneous complex IV gave a lower yield (Run 1). Both the addition of MsOH (methanesulfonic acid) and the presence of silica in the reaction slightly increased the activity (Runs 2-3). In all cases, NMR analysis of the reaction solution using complex IV indicated the formation of the colored, inactive dimeric species V (Runs 1-3).

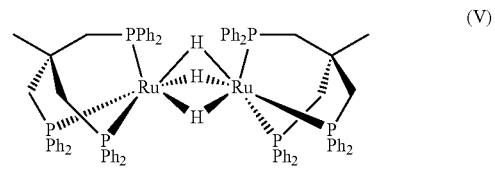

(V)

This data suggest that site isolation is a factor in the increased activity of catalyst III-b.

Example 4

Long-Term Stability Study of Catalyst III-b

The long-term stability of catalyst III-b in the hydrogenolysis of 2-piperidone was tested by recycling and substrate-addition experiments using the general hydrogenolysis procedure above.

For the recycling experiments, the catalyst suspension was removed from the autoclave, centrifuged, washed, and reused with new substrate solution. Each cycle was performed with 1 mol % catalyst III-b (0.06 mmol/g on amorphous silica), 1.0 mmol 2-piperidone, 2.0 mL THF, for 16 h at 160° C. with 100 bar H₂ at room temperature (SI 1.1).

In the substrate-addition experiments, after the desired reaction time, a sample was taken, and more substrate solution was added.

The results of these experiments are graphically depicted in the FIGURE.

As seen from the FIGURE, both experiments showed that the catalyst can be reused after catalysis, with the recycling experiment having a slightly higher activity than the addition test.

During the long-term stability experiments, activity during runs four and five was lower than the previous stages. In prior experiments, formation of the inactive complex [(Triphos)Ru(CO)(H)₂] VI was observed under catalytic conditions, which can be reactivated by protonation with added acids.

(VI)

[Structure VI: Ru complex with three PPh₂ ligands bound to a bicyclic phosphine cage, plus two H ligands and CO]

To test if the catalyst activity can be regenerated, after the fifth recycling experiment, three equivalents of MsOH were added to the reaction mixture. As seen from the FIGURE, adding MsOH increased the catalytic performance in both cases. The leaching rates at each step were low with the first run of the recycling experiment being the highest (0.38 ppm, 0.16% total Ru; SI, 6).

After the last recycling run, the catalyst material was recovered, dried, and analyzed via scanning transmission electron microscopy (STEM). Minor formation of nanoparticles on the catalyst surface (SI, 7.1 and 7.2) was observed.

In order to determine when the nanoparticles are formed, the recycling experiment was repeated in the presence of anisole as a co-substrate. Ruthenium nanoparticles are known to hydrogenate anisole quickly under the reaction conditions. Thus, formation of methoxycyclohexane during catalysis would indicate the formation of nanoparticles on the catalyst surface. Between the second and last catalytic runs, only minor traces of methoxycyclohexane (less than one TON) were observed. This confirms that the nanoparticles play little to no role in the catalytic properties of catalyst III-b (SI, 7.3 and 7.4).

In a separate experiment, it was observed that the overall activity of the catalyst decreased in the presence of the product piperidine, which inhibits the catalyst by blocking coordination sites (SI, 5). Thus, higher activity can be achieved by removal of the product, as in the recycling study or during a flow reaction.

The invention has been described in detail with particular reference to specific embodiments thereof, but it will be understood that variations and modifications can be made within the spirit and scope of the invention.

We claim:

1. A compound having the structure of formula (I):

[Structure I: (EtO)₃Si-CH₂CH₂CH₂-O-CH₂-C(CH₂PPh₂)₃]

2. A method for preparing the compound of claim 1, the method comprising:
   (a) reacting pentaerythritol tribromide with allyl iodide in the presence of a base to form an ether compound having the structure of formula (A):

[Structure A: allyl-O-CH₂-C(CH₂Br)₃]

(b) reacting the ether compound (A) with triethoxysilane in the presence of a platinum-N-heterocyclic carbene (Pt—NHC) catalyst to form a silyl ether compound having the structure of formula (B):

[Structure B: (EtO)₃Si-CH₂CH₂CH₂-O-CH₂-C(CH₂Br)₃]

(c) reacting the silyl ether compound (B) with potassium diphenylphosphide to form the compound of formula (I).

3. The method of claim 2, wherein the Pt—NHC catalyst has the structure of formula (C):

[Structure C: Pt-NHC catalyst with 2,6-diisopropylphenyl groups on imidazolidinylidene, coordinated to Pt and a divinyltetramethyldisiloxane ligand]

4. A compound having the structure of formula (II):

[Structure II: (EtO)₃Si-CH₂CH₂CH₂-O-CH₂-C(CH₂PPh₂)₃Ru-L]

wherein L represents a ligand selected from trimethylenemethane, allyl, methylallyl, ethylene, cyclooctadiene, acetylacetonate, and acetate.

5. The compound of claim 4, wherein L is trimethylenemethane.

6. A method of preparing the compound of claim 4, which comprises reacting a compound having the structure of formula (I):

(I)

[Structure I: (EtO)₃Si-CH₂CH₂CH₂-O-C(CH₂PPh₂)₃]

with a Ru-containing compound selected from Ru(acac)₃, [Ru(COD)(methylallyl)₂], Ru(NBD)(methylallyl)₂, Ru(ethylene)₂(methylallyl)₂, [(COD)RuCl₂]ₙ, RuCl₃, [(PPh₃)₃Ru(H)(CO)Cl], and [(cymanthren)RuCl₂]₂.

7. The method of claim 6, wherein the Ru-containing compound is [Ru(COD)(methylallyl)₂].

8. A catalyst composition comprising:
(a) an oxidic support; and
(b) the compound of claim 4 immobilized on the support.

9. The catalyst composition of claim 8, wherein the oxidic support comprises silica, magnesia, titania, or alumina.

10. The catalyst composition of claim 8, wherein the oxidic support comprises silica.

11. The catalyst composition of claim 8, wherein L is trimethylenemethane.

12. A process for hydrogenolysing an amide, the process comprising:
contacting an amide with hydrogen in the presence of a catalyst composition at conditions effective to form an amine and optionally an alcohol,
wherein the catalyst composition comprises:
(a) an oxidic support; and
(b) a compound immobilized on the support, the compound having the structure of formula (II):

(II)

[Structure II: Ru complex with tripodal triphosphine ligand and ligand L]

wherein L represents a ligand selected from trimethylenemethane, allyl, methylallyl, ethylene, cyclooctadiene, acetylacetonate, and acetate.

13. The process of claim 12, wherein the oxidic support comprises silica, magnesia, titania, or alumina.

14. The process of claim 12, wherein the oxidic support comprises silica.

15. The process of claim 12, wherein L is trimethylenemethane.

16. The process of claim 13, wherein L is trimethylenemethane.

17. The process of claim 14, wherein L is trimethylenemethane.

18. The process of claim 12, wherein the amide comprises a lactam.

19. The process of claim 13, wherein the amide comprises a lactam.

20. The process of claim 17, wherein the amide comprises a lactam.

* * * * *